United States Patent [19]
Luciano

[11] 3,966,808
[45] June 29, 1976

[54] MANUFACTURE OF 6-METHYLENETETRACYCLINES

[75] Inventor: Franco Paolo Luciano, Trezzano sul Navigiio (Milan), Italy

[73] Assignee: Rachelle Laboratories Italia, S.p.A., Milan, Italy

[22] Filed: July 9, 1975

[21] Appl. No.: 594,291

Related U.S. Application Data

[63] Continuation of Ser. Nos. 480,833, June 19, 1974, abandoned, and Ser. No. 192,336, Oct. 26, 1971, abandoned, and a continuation-in-part of Ser. No. 101,688, Dec. 28, 1970, abandoned.

[52] U.S. Cl. .......................................... 260/559 AT
[51] Int. Cl.[2] ....................................... C07C 103/19
[58] Field of Search ............................. 260/559 AT

[56] References Cited
UNITED STATES PATENTS
3,109,007  12/1963  Blackwood et al. ........... 260/559 AT Primary Examiner—C. Davis
Attorney, Agent, or Firm—Hubbell, Cohen, Stiefel & Gross

[57] ABSTRACT

Methacycline (6-methylene-5-oxytetracycline) is prepared by halogenating oxytetracycline (5-hydroxytetracycline) to produce the 11a-halo-6,12-hemiketal, under conditions which form and maintain the product in the enolic form, reacting the hemiketal base with acid to produce the hemiketal acid salt, dehydrating the acid salt to form 11a-halo-6-methylene-5-oxytetracycline, and reducing the compound to the salt of 6-methylene-5-oxytetracycline. An improved method for producing the 6-methylenetetracycline base from the product salt is also disclosed. The process is applicable to the synthesis of 6-methylenetetracycline per se or other 6-methylenetetracyclines, as well as methacycline.

4 Claims, No Drawings

3,966,808

MANUFACTURE OF 6-METHYLENETETRACYCLINES

RELATED APPLICATIONS

This application is a continuation of applications Ser. No. 480,833 filed June 19, 1974 and Ser. No. 192,336 filed Oct. 26, 1971, both of which are now abandoned; and a continuation-in-part of prior application Ser. No. 101,688 filed Dec. 28, 1970 and also now abandoned.

BACKGROUND OF THE INVENTION

Blackwood et al, in U.S. Pat. No. 2,984,686, assigned to Chas. Pfizer & Co., Inc. and issued May 16, 1961, disclose the production of 6-methylene-5-oxytetracycline and its 7-halo derivatives; the same procedure is shown for other tetracyclines by Blackwood et al, with one further collaborator, in the Journal of the American Chemical Society, Vol. 85 (1965) at pages 3943 to 3953. All of the products have antibiotic properties of varying degree, generally being at least as strong as the starting product; 6-methylene-5-oxytetracycline is particularly useful, possessing better properties than the initial reactant, oxytetracycline.

Blackwood et al's basic process involves (1) 11ahalogenation of a tetracycline, either in base or salt form, to produce an 11a-halo-6,12-hemiketal; (2) dehydration of the hemiketal to the 11a-halo-6-methylene derivative; and (3) reduction of this halo-methylene derivative, in the salt form, to the end product. The process as described is characterized by low overall yields, resulting in high costs.

OBJECT OF THE INVENTION

The principal object of this invention is the production of 6-methylene-5-oxytetracycline and other 6-methylenetetracyclines, of high purity and biological potency, in substantially higher yields and at lower costs than with prior art methods.

SUMMARY OF THE INVENTION

It has now been found that 6-methylene-5-oxytetracycline and other 6-methylenetetracyclines can be prepared in substantially higher yields and purities than heretofore, by halogenating the 5-oxytetracycline or other tetracycline reactant under conditions sufficient to spontaneously precipitate the 11a-halo-6,12-hemiketal base in the enolic form and converting the hemiketal base to the hemiketal acid salt, prior to dehydrating the latter material to the corresponding 6-methylene compound. This is accomplished by conducting the halogenation of a solution of the tetracycline base or salt at a sub-ambient temperature, while maintaining the pH between about 3.0 and 5, to spontaneously initiate precipitation of the enolic form of the hemiketal, then reacting the hemiketal to produce the hemiketal acid salt at temperatures from −10° to 20°C., crystallizing the hemiketal acid salt in the enolic form, and dehydrating the salt to form 11a-halo-6-methylene5-oxytetracycline or the corresponding derivatives of other 6methylenetetracyclines. The 11a-halo intermediate may then be dehalogenated in known fashion to the deshalogenated 6-methylene compound. Alternatively, the 11-a-halo- 6-methylene compounds may be directly hydrogenated to form the corresponding biologically active 6-deoxytetracyclines (e.g., doxycycline).

In accordance with a further feature of this invention, the free base form of the final 6-methylenetetracycline product may be prepared in substantially higher yields and in greater purity than by hiterto known methods, by neutralizing an aqueous solution of the salt at about 50° to 90° C. to the neutral point (pH about 6.5 to 7.5 at ambient temperatures about 20°C.) with suitable alkali. The elevated temperature, combied with the control of pH, insures recovery of the free base in superior yield and purity.

While the present invention is principally described herein in terms of the conversion of oxytetracycline to methacycline it will be understood that it is also applicable to the production of other 6-methylenetetracyclines from the corresponding tetracylines. Accordingly, the following description of the preferred parameters utilized in the syntheses of methacycline should be regarded as illustrative rather than limiting. Further, all parts and percentages referred to in the following description are given by weight unless otherwise indicated.

As indicated hereinabove, the principal elements of the present invention comprise the spontaneous precipitation of the 11a-halo hemiketals, and the subsequent conversion of such materials to the corresponding hemiketal acid salts prior to dehydration to form the 11a-halo-6-methylenetetracyclines therefrom. It is most desirable to produce the 11-a-halo-6,12-hemiketals in the enolic rather than in the ketonic form (viz., that incorporating a free ketone group at C-12). Such is the case since the latter form does not crystallize, is therefore difficult to recover and moreover, is subject to appreciable degradation.

It has been found that the 11a-halo hemiketals formed in accordance with the previously described Blackwood et al technique contain substantial impurities in the undesirable ketonic form, as evidenced by the determination of infrared absorption bands below 6 microns in materials so produced. The spontaneous precipitation of the hemiketals in the enolic form without co-production of substantial amounts of the soluble ketonic form, and the stabilization of the enol during the subsequent dehydration reaction are, therefore, important elements of the present invention.

In particular, it has been found that the 11a-chloro-5-oxytetracycline-6,12-hemiketal base, prepared as described in Example XV of the aforesaid Blackwood et al patent by halogenation in 1,2-dimethoxyethane and precipitation in water, exhibits an infrared absorption band below 6 microns thus indicating the presence of the ketonic form of the desired hemiketal. When, on the other hand, the 11a-halogenation is conducted at the particular temperature and acidity conditions specified hereinabove, the enolic form of the hemiketal spontaneously crystallizes, even in the presence of an aqueous solvent medium. Infrared analysis of the product thus produced shows no carbonyl absorption and thus confirms formation of the enol to the substantial exclusion of the undesirable ketonic material.

It has been further found that conversion of the enolic form of the hemiketal base thus produced to the corresponding hemiketal acid salt, e.g., the hydrochloride, prior to dehydration to the 11a-halo-6-methylenetetracycline, increases both the yield and purity of the product subsequently recovered. Thus, the enolic form of the hemiketal salt possesses markedly higher stability than the corresponding carbonyl compound to attack by the hydrogen fluoride or other strong acid which may be used to dehydrate the hemiketal material. Moreover, the hemiketal salt may be recovered in higher purities than the hemiketal base as a result of the differing solubility characteristics thereof. The formation of the hemiketal salt in the synthesis reaction is, therefore, a further important aspect of the present invention.

As indicated hereinafter, methacycline hydrochloride has been prepared by the procedures described in Examples I, II and XV of the aforesaid Blackwood et al patent, obtaining such product in yields (based upon the weights of oxytetracycline base reacted and methacycline hydrochloride recovered) of only from 25–29%. On the other hand, when methacycline hydrochloride was prepared by the spontaneous precipitation of the hemiketal base in the enolic form and the subsequent conversion of such base to the hemiketal hydrochloride prior to dehydration and 11a-dehalogenation, yields of from about 45-49% were achieved. Such difference in yields is particularly important in those instances in which it may be desired to further convert the methacycline product to doxycycline ($\alpha$-6-deoxy-5-oxytetracycline).

PREFERRED EMBODIMENTS OF THE INVENTION

The preferred mode of carrying out the method of the invention is described below; such description may be considered in the light of the attached drawing, incorporating a flow sheet of the synthesis (illustrated in general terms on the left-hand side of the drawing in connection with one preferred embodiment of the invention on the righthand side thereof).

As indicated hereinabove, the raw material utilized in the present synthesis is a tetracycline, e.g., oxytetracycline. Such material may be used as the free base, or in the salt form. Oxytetracycline base, for example, is insoluble in 1,2-dimethoxyethane or similar polar solvents. It should first be solubilized by refluxing in an apolar solvent such as tetrahydrofuran, acetone or dioxane; the small amount of insolubles are filtered off, and the base recovered from solution. The tetracycline base may then be dissolved in an organic solvent, e.g., a saturated monohydric alcohol having from about 1 to 5 carbon atoms, suitably isopropanol; a ketone having from 3 to 10 carbon atoms, suitably acetone; dioxane; tetrahydrofuran; or a lower alkyl ether of ethylene or diethylene glycol, suitably isopropyl glycol.

When the tetracycline reactant is employed in the salt form, e.g., as oxytetracycline hydrochloride in the case of the synthesis of methacycline, such material may suitably be dissolved in an aqueous solvent system. Such systems may include mixtures of any of the above organic solvents with water, particularly good results having been obtained with mixtures of varying proportions of isopropyl glycol and water. In the case of the production of methacycline it has been found that higher yields of the hemiketal may be obtained by the halogenation of oxytetracycline hydrochloride rather than oxytetracycline base; accordingly, it is particularly preferred to utilize the acid salt reactant in such synthesis.

The tetracycline reactant, whether in the base or salt form and whether in an anhydrous or aqueous reaction medium, is halogenated in accordance with the present invention under conditions designed to produce the hemiketal base in the enolic form to the exclusion of the ketonic form thereof. For this purpose the reaction mixture is maintained at sub-ambient temperatures, preferably below about 0° C., and desirably from about −15° to −4° C., while the acidity of the reaction mixture is regulated to between about pH 3.0 and 5.0, best results being achieved at pH values of from about 4 to 4.5 (which approximate the isoelectric point of the mixture). It has been determined that these conditions are critical to produce the enolic form of the hemiketal base. Since the enol possesses a higher free energy than the corresponding ketonic form and is, therefore, inherently less stable, the low reaction temperature must be maintained. Similarly, control of the acidity of the reaction mixture is required to prevent formation of the carbonyl moiety.

The 11a-halogenation of the tetracycline base or acid salt may be effected by any halogenating agents conventionally employed in the art including, for example, those chlorinating agents described in the aforesaid Blackwood et al patent. Halogenating agents which may be so utilized include chlorine; N-chloro lower alkanoic acid amides, e.g., N-chloroacetamide; hydrocarbon dicarboxylic acid imides, e.g., N-chlorosuccinimide, phthalimide and the like; N-lower-alkanoylanilides, e.g., N-chloroacetanilide, propionanalide and the like; 3-chloro and 3,5-dichloro, 5,5-dimethylhydantoin and the corresponding bromo-substituted hydantoins; pyridinium perchloride hydrohalides, e.g., pyridinium perchloride hydrochloride and lower alkyl hypochlorites, e.g., t-butylhypochlorite. Particularly satisfactory results have been obtained by the use of the hydrocarbon dicarboxylic acid imides, such as N-chlorosuccinimide, as the halogenating agent.

The reaction is suitably conducted with a slight excess of the halogenating agent, generally from about 10% to 80% over theoretical. In the case of the halogenation of a tetracycline base with N-chlorosuccinimide in an anhydrous reaction medium from about 1.1 to about 1.4 moles, preferably about 1.25 moles, of the halogenating agent are reacted per mole of base. On the other hand, in the case of the halogenation of tetracycline acid salts in aqueous media it is necessary to correct for hydrolysis of the halogenating agent by neutralizing the haloacid thus formed. Thus, in the reaction of N-chlorosuccinimide with oxytetracycline hydrochloride from about 1.5 to 1.8 moles, preferably about 1.7 moles, of the N-chlorosuccinimide are employed per mole of oxytetracycline hydrochloride, and from about 2.4 to about 2.6 moles, preferably about 2.5 moles, of an organic base, e.g., triethylamine or N,N'-dimethylformamide, are utilized to correct the acidity of the solution to about pH 4-4.5.

For optimum results it is also desirable, when halogenating a tetracycline base, to utilize reaction mixtures incorporating at least 2.9 moles of the base per liter of solution reacted. It has been found that higher product yields are obtained when such reactants are employed as compared, for example, with the relatively lower concentration reaction mixtures referred to in the aforesaid Blackwood et al patent.

After spontaneous crystallization of the enolic form of the hemiketal base is initiated, the reaction mixture is filtered, water or ethyl ether, for example, being added to assist with the filtration if desired, and the product recovered for further reaction.

As previously indicated, the hemiketal base is thereafter converted to the corresponding hemiketal acid salt, e.g., the hydrochloride, the sulfosalicylate, or the p-toluene sulfonate, to stabilize the enol and to facilitate recovery of the product in high purities. The hemiketal salt is crystallized from a solution of the base in a solvent, e.g., a low boiling alcohol such as methanol, ethanol or isopropanol, by reaction with the appropriate acid, e.g., hydrochloric acid. The use of gaseous hydrogen chloride in 5% to 15% concentrations in methanol has been found suitable for this purpose.

The salt-forming step is conducted at temperatures at or below ambient temperatures, suitably between about 5° C. and 20° C., and the crystallization is completed within a relatively short period of time, e.g., within from about 2–3 hours. The use of higher temperatures or substantially higher acid concentrations provokes the opening of the oxygen bridge and the formation of the undesired ketonic material.

By converting the hemiketal base to the hemiketal hyddrochloride or other acid salt prior to dehydrating the same to the 11a-halo-6-methylenetetracycline intermediate, the final product may be recovered in substantially higher yields and purities than heretofore possible. The improved results thus obtained are demonstrated in the experiments described below. It is believed that improved product yields and purities are achieved by formation and reaction of the hemiketal acid salt since the ketal bridge of such material is more stable to thermal attack in the subsequent dehydration reaction than is the corresponding bridge of the hemiketal base. Moreover, dehydration of the hemiketal acid salt is less exothermic than dehydration of the hemiketal base. It will, however, be appreciated that the reaction mechanism postulated should not be construed as limiting, but only as a possible explanation, in part, of the improved results obtained in accordance herewith.

After recovering the hemiketal hydrochloride, as by filtration, it is dehydrated to form the 11a-halo-6-methylenetetracycline, e.g., 11a-chloro-6-methylene-5-oxytetracycline. The hemiketal hydrochloride may thus be treated with a strong, dehydrating acid such as trifluoroacetic or hydrofluoric acid, the latter being preferred. Employing hydrofluoric acid, the dehydration is carried out at temperatures of from about −10° to +19° C., preferably from about −5° to +5° C., for periods of from about 3–4 hours. The dehydrating acid is reacted in excess, in an amount of three times the weight of the hemiketal hydrochloride when, for example, hydrofluoric acid is utilized.

The 11a-chloro-6-methylene product may be recovered directly as the hydrofluoride salt or alternatively as, for example, a perchlorate, hydrochloride, p-toluene sulfonate, or sulfosalicylate salt. Preferably, the dehydrated material is recovered as the perchlorate, e.g., by reacting perchloric acid with the dehydration reaction mixture and crystallizing the perchlorate salt therefrom. The perchloric acid is reacted in excess of that stoichiometrically required for salt formation, desirably in about twice such amount. Suitably the resulting aqueous solution of perchloric acid is cooled to about 5°C. prior to combining with the dehydration reaction mixture. Upon combining such materials and agitating the resulting mixture the perchlorate salt precipitates and may be separated and recovered by filtration or otherwise.

It is also feasible, as noted above, to recover the hydrofluoride salt formed in the dehydration reaction as such, if so desired. In this instance the 11a-chloro-6-methylene material may be precipitated from a suitable cold non-solvent, e.g., ethyl or isopropyl ether, maintained at temperatures below 0° C. The product may thereafter be separated from the solvent by filtration or the like and washed with ether or other non-solvent to remove any remaining acid.

As previously indicated, it is particularly preferred to recover the 11a-chloro-6-methylene product as the perchlorate, since such material readily precipitates in pure crystalline form as compared, for example, with the fluoride salt recovery by addition of an ether or other nonsolvent. Moreover, formation of the perchlorate obviates the necessity for the addition of an ether, thus decreasing the volumes of volatile liquids to be handled and, consequently, improving the safety and economy of operation.

Whichever 11a-chloro-6-methylenetetracycline salt is, however, recovered, such material may subsequently be reduced to remove the 11a-halogen and produce methacycline in the manner known in the art. The 11a-dehalogenation may be effected with any standard reducing agent including an alkali metal hydrosulfite, e.g., sodium hydrosulfite in aqueous media; an active metal, e.g., zinc or iron in a mineral acid such as dilute hydrochloric acid; or sodium iodide in a halogen-acceptor solvent, e.g., acetone or methanol, and preferably in the presence of zinc metal. The reduction is suitably carried out in solution in an aqueous medium incorporating a water-miscible solvent, e.g., the isopropyl ether of ethylene glycol, with sufficient acid present in the medium to maintain the same at pH values within the range of from about 1.5-6.5, preferably from about 4.5–5. The reducing agent, desirably sodium hydrosulfite, is reacted with the 11a-halo-6-methylenetetracycline in amounts of from about 1.1 to 1.5 moles, desirably about 1.2 moles, per mole of the latter.

The reaction mixture containing the dehalogenated product, e.g., methacycline, is, desirably, then brought to a pH of from about 7.5 to 7.7 to completely solubilize the 6-methylenetetracycline and facilitate separation of sulfur or other impurities formed therein. The bioactive material may thereafter be precipitated from the reaction mixture as the acid salt by the addition of excess acid, e.g., hydrochloric acid, and the product recovered, e.g., by filtration or the like.

In accordance with a further feature of the invention the methacycline hydrochloride or other 6-methylenetetracycline acid salt may be converted to the corresponding free base in substantially higher yield and greater purity than heretofore possible by neutralizing an aqueous solution of the salt at temperatures within the previously indicated range of from about 50°–90° C., preferably at temperatures of from about 60°–70° C., and at pH values of from about 6.5–7.5, desirably from about 6.7–7.2. The salts may be neutralized with alkali metal hydroxides, carbonates or bicarbonates or with suitable organic bases, the use of any desired alkaline material being permissible so long as the neutralization is carried out in aqueous medium at the temperature and acidity conditions specified hereinabove.

As noted in Examples V and VI below, it has been found that tetracycline bases produced in this manner may be recovered in yields of from about 84–87% and conversions of from about 91–94%, and with chemical assays of from about 96–97%, whereas bases recovered by the neutralization technique described, for example, in the aforesaid Blackwood et al J.A.C.S. article may only be obtained in yields of from about 40–45% and conversions of from about 43.4–48.6%, and with chemical assays of about 89%. The present technique thus additionally provides a markedly improved procedure for converting the 6-methylenetetracycline acid salts to the corresponding free bases, whether such salts have been prepared from the corresponding tetracyclines by the synthesis described hereinabove or by a previously known technique.

The following examples illustrate preferred forms of the present method for the synthesis of methacycline from oxytetracycline, and evidence the marked differences between the process of this invention and previously described syntheses of 6-methylenetetracyclines. It should be understood that the preferred embodiments of the invention described hereinafter are illustrative and are not to be construed in a limiting sense.

As used in the following Examples or otherwise specified herein, the percentage yield refers to the weight of product formed as a percentage of the weight of the initial reactant, whereas the percentage conversion refers to the amount of product formed as a percentage of the amount of product theoretically producible by stoichiometric reaction. As further specified, the percentage purity refers to the "titer", viz., the weight percent of the particular tetracycline in the material analyzed, calculated as the base (U.S. Code of Federal Regulations, Title 21, Part 148y).

EXAMPLE I

METHACYCLINE HYDROCHLORIDE FROM OXYTETRACYCLINE HYDROCHLORIDE a. Preparation of Hemiketal Base 250 grams of oxytetracycline hydrochloride were dissolved in a mixture of 2500 ml of water and 2500 ml of the isopropyl ether of ethylene glycol at a temperature of −8° C. After dissolution, 90 ml of triethylamine were added, and immediately after 110 grams of N-chlorosuccinimide were added to adjust the pH to 4–4.5. Strong agitation was maintained for 10 minutes; spontaneous precipitation of product started in two minutes. After 10 minutes, when precipitation seemed complete, 12.5 liters of water were added to facilitate filtration, and the product was recovered. Yield 198 g. (79.3%).

There were no infrared absorption bands below 6 microns; U.V. in methanol, 0.01 N HCl = λ 266 and λ 345, identifying the product as the enolic form of 11a-chloro-5-oxytetracycline-6,12-hemiketal.

b. Preparation of Hemiketal Hydrochloride 60 grams of the hemiketal base thus prepared were dissolved in 180 ml of anhydrous methanol containing 10% HCl; the temperature was maintained at 10° C. The product was crystallized; yield 43 grams of the hemiketal hydrochloride.

c. Preparation of Methacycline Hydrochloride

The hemiketal hydrochloride thus formed was added to 130 ml of anhydrous HF at −5° C., and stirred for 4 hours. The reaction mixture was then treated with 1300 ml of isopropyl ether, agitated, and filtered, 43 grams of 11a-chloro-6-methylene-5-oxytetracycline hydrofluoride being recovered.

42 grams of the dehydrated product thus formed was dissolved in a mixture of 168 ml of the isopropyl ether of ethylene glycol, 84 ml of water and 4.2 ml of 37% hydrochloric acid. To this was added a solution of 21 grams of sodium hydrosulfite in 84 ml of water. After 3 hours of agitation, triethylamine was added in an amount sufficient to adjust the pH of the mixture to 7.5 and the solution was filtered. The filter cake was then washed with 42 ml of a mixture of equal proportions of water and the isopropyl ether of ethylene glycol. To the filtrate, 176 ml of concentrated hydrochloric acid were added, and the mixture stirred for 3 hours while maintaining it at a temperature of 5° C. The methacycline salt crystallized, was filtered, and washed with isopropanol and acetone. Yield 29 grams (48.5% based on the hemiketal). Biological assay 865 mcg/mg; chemical assay 91.3% (expressed as methacycline base). Infrared analysis confirmed a structure consistent with that of methacycline hydrochloride.

EXAMPLE II

METHACYCLINE HYDROCHLORIDE FROM OXYTETRACYCLINE HYDROCHLORIDE a. Preparation of Hemiketal Hydrochloride 198 grams of the hemiketal base prepared as described in Example I were dissolved in 590 ml of anhydrous methanol containing 10–12% HCl. The mixture was stirred and maintained at a pH of about 1 and at a temperature of 5° C. to effect crystallization of the hemiketal hydrochloride. The latter was recovered by filtration in an amount of 177.3 grams (71% yield based upon the initial oxytetracycline hydrochloride reacted).

b. Preparation of Methacycline Hydrochloride 177 grams of the hemiketal hydrochloride thus produced was added to 500 ml of anhydrous hydrogen fluoride at −5° C. and stirred for 4 hours. The reaction mixture was then treated with 5000 ml of isopropyl ether, agitated and filtered, 174.9 grams of 11a-chloro-6-methylene-5oxytetracycline hydrofluoride being recovered.

The dehydrated product thus formed was dissolved in a mixture of 700 ml of isopropyl ether of ethylene glycol, 350 ml of water and 17.5 ml of 37% hydrochloric acid. To this was added a solution of 87.5 grams of sodium hydrosulfite in 350 ml of water. After 3 hours of agitation, triethylamine was added in an amount sufficient to adjust the pH of the mixture to 7.5 and the solution was filtered. The filter cake was then washed with 175 ml of a mixture of equal proportions of water and isopropyl ether of ethylene glycol. To the filtrate, 745 ml of concentrated hydrochloric acid were added, and the mixture stirred for 3 hours while maintaining it at a temperature of 5° C. The methacycline salt crystallized, was filtered, and washed with isopropanol and acetone. Yield 121 grams (48.5% based on the oxytetracycline hydrochloride). Biological assay 865 mcg/mg; chemical analysis 91.5% (expressed as methacycline base); humidity (K.F.) of 0.5%.

EXAMPLE III

PREPARATION OF THE HEMIKETAL BASE FROM OXYTETRACYCLINE BASE

The hemiketal base may be prepared from oxytetracycline base rather than an oxytetracycline salt, as follows:

46 grams of oxytetracycline base, pretreated by reflux in dioxane, were dissolved in 350 ml of 1,2-dimethoxyethane at −5° C., and 16 grams of N-chlorosuccinimide were admixed while maintaining the temperature at −5° C. Acidity was equal to pH 3–4 (apparent value in anhydrous solvent). After 2½ minutes, the product started to crystallize. Stirring was maintained for several minutes; the product was filtered, washed with more 1,2-dimethoxyethane, and dried. Yield 21 grams (45.6%).

Upon infrared analysis (KBr at 1% concentration) the product did not exhibit any absorption bands below 6 microns; U.V. in methanol, 0.01 N HCl = λ 216, λ 234. The product was thus identified as the enolic form of 11a-chloro-5-oxytetracycline-6,12-hemiketal.

EXAMPLE IV

RECOVERY OF THE 11a-HALO-6-METHYLENETETRACYCLINE SALT AS THE PERCHLORATE

A further quantity of methacycline hydrochloride was formed from the hemiketal hydrochloride made in accordance with Example II above, by the following operations in which the 11a-chloro-6-methacyclinetetracycline salt formed by dehydration of the hemiketal hydrochloride was recovered as the perchlorate.

Initially, 100 grams of the hemiketal hydrochloride made as described above was added to 300 ml of anhydrous hydrogen fluoride at −5° C. and stirred for 4 hours. Concurrently, 60 ml of 70% perchloric acid was mixed in 900 ml of water. The two solutions were combined: the temperature of the combined perchloric-fluoric acid solution raised to between 50°– 60° C., and it was thereafter cooled with agitation to 5° C. Product crystallized rapidly from the solution was separated by filtration. The crystals were washed and dried, 78.5 grams of 11a-chloro-6-methylene-5-oxytetracycline perchlorate resulting.

The dehydrated perchlorate product thus formed was further reduced to methacycline hydrochloride in the manner described in Example II.

EXAMPLE V

METHACYCLINE BASE FROM METHACYCLINE HYDROCHLORIDE 5 grams of methacycline hydrochloride were mixed with 0.54 grams of anhydrous sodium carbonate. The mixture was slowly added, with stirring, to 25 ml of water maintained at a temperature of 60°–70° C. The mixture was maintained at such temperature, with agitation, for from 10 to 15 minutes after completion of the addition of the methacycline hydrochloride-sodium carbonate mixture thereto. The mixture was then cooled to 5° C. and held at such temperature, with agitation, for a further hour. The resulting suspension had a pH of 6.7–7.2. It was filtered and the product washed with water.

The dry methacycline base thus produced weighed 4.25 grams, had a titer (based on methacycline base) of 97.8% and a humidity (K.F.) of 3.89%. The product was thus produced in a yield of 85%, equivalent to a conversion of 90.5%.

EXAMPLE VI

METHACYCLINE BASE FROM METHACYCLINE HYDROCHLORIDE

5grams of methacycline hydrochloride (98%) were added to 25 ml of water, and the mixture heated to a temperature of 60°–70° C. The mixture was agitated and triethylamine added thereto to a final pH of 6.7 –7.2. Agitation was continued for a further 10–15 minutes and the solution was simultaneously cooled to +5° C. The suspension was then permitted to stand for an hour, after which it was filtered, the product being washed with cold water.

The dry methacycline base thus produced weighed 4.38 grams, had a titer (based on methacycline) of 96.6% and a humidity (K.F.) of 4.33%. The product was thus produced in a yield of 87.5%, equivalent to a conversion of 92%.

For purposes of comparison, and employing the same methacycline hydrochloride utilized in Examples V and VI, methacycline base was prepared in the manner described at 85 J.A.C.S., 3950, column 2, lines 15–20.

Specifically, 5 grams of the methacycline hydrochloride (98% titer) were dissolved in 150 ml of methanol and 4 ml of water containing 1.42 ml of triethylamine. After stirring for a brief period the solution was immediately filtered. The product crystallized over night at 5° C. and was thereafter recovered by filtration and washed with methanol and cold water.

The dry methacycline base thus produced weighed 2.36 grams, had a titer (based on methacycline base) of 88.6% and a humidity (K.F.) of 5.02%. The product was thus produced in a yield of 47%, equivalent to a conversion of 45.5%.

METHACYCLINE HYDROCHLORIDE BY SPONTANEOUS CRYSTALLIZATION OF HEMIKETAL BASE, WITHOUT FORMATION OF HEMIKETAL HYDROCHLORIDE

Example I was repeated, using an identical 60 grams of hemiketal base as the initial reactant, and omitting the intermediate step involving preparation of the hemiketal salt. The subsequent dehydration and reduction steps were carried out on the 60-gram sample of hemiketal base employing, however, approximately 1.5-fold the amount of each reagent specified therein. There were thus obtained 22 grams of methacycline hydrochloride product (36.7% yield based on the hemiketal base) having a biological assay of 860 mcg/mg and a chemical assay of 88.5%, expressed as methacycline base.

METHACYCLINE HYDROCHLORIDE BY PARTIAL CRYSTALLIZATION OF HEMIKETAL BASE, FOLLOWED BY FORMATION OF HEMIKETAL HYDROCHLORIDE a. Preparation of Hemiketal Base For purposes of comparison the hemiketal base, pretreated by refluxing as indicated in Example IV, was prepared in the manner described in part in Example XV of Blackwood et al Pat. No. 2,984,686 by dissolving 9.2 grams of anhydrous oxytetracycline base in 100 ml of 1,2-dimethoxyethane, followed by the addition of 3.2 grams of N-chlorosuccinimide. The mixture was stirred for 3 minutes, and the crystallized portion recovered by filtration. 2.1 grams of product (m.p. 180° C., yield 22.8%) were thus recovered which did not show any I.R. absorption bands prior to 6 microns. The product exhibited ultraviolet peaks (in 0.01 N HCl in methanol) at λ264 and λ344.

The mother liquor obtained by filtration was poured into 0.400 liters of water, 2grams of further product (m.p. 180° C.) being separated and recovered by filtration therefrom. The additional product (m.p. 180° C.) showed carbonyl I.R. absorption at 5.65 microns. U.V.

peaks were exhibited at λ266 and λ345. The total yield of hemiketal base, in both enol and ketone forms was 4.1 grams (44.5%).

b. Preparation of Hemiketal Hydrochloride 20 grams of hemiketal base prepared in the preceding manner were dissolved in 60 ml of anhydrous methanol containing 10% HCl. The mixture was maintained at 20°–22° C. and at a pH of about 1 to permit crystallization of the hemiketal acid salt. The hydrochloride was recovered by filtration, 18 grams being recovered after washing and drying the filter cake.

c. Preparation of Methacycline Hydrochloride 18 grams of the hemiketal hydrochloride were admixed with 54 ml of anhydrous hydrogen fluoride at −5° to 5° C. and agitated for 3.5 hours. The reaction mixture was then treated with 540 ml of isopropyl ether at 0° C. to precipitate the 11a-chloro-6-methylenetetracycline intermediate. The product was separated by filtration, and washed with further ether to remove the remaining acid. 18 grams of the dehydrated product, as the hydrofluoride, were thus obtained.

18 grams of the intermediate were thereafter reduced in a mixture containing 72 ml isopropyl ether of ethylene glycol, 36 ml water and 1.8 ml of HCl (37%), to which 9 grams of sodium hydrosulfite in 36 ml of water were first added. The reaction mixture was maintained at a temperature of 20° C. for a period of 3 hours. Triethylamine was added to the stirred mixture during such period to adjust the pH to 7.5.

The reaction mixture was then filtered and 75 ml of concentrated HCl were added to the filtrate to precipitate the desired dehalogenated 6-methylenetetracycline product as the hydrochloride. After 3 hours, the product was recovered by filtration, and washed with isopropanol and acetone. 14.4 grams of product (melting point 203° C., chemical assay 91.3%, and biological assay 865 mcg/mg were thus obtained; 32% total yield (w/w).

BLACKWOOD ET AL EXAMPLE XV

The hemiketal base prepared in the manner described in Example XV of Blackwood et al U.S. Pat. No. 2,984,686 (as indicated in the above experiment) was further converted to methacycline hydrochloride by the procedures described in Examples I and II of the said Blackwood et al patent (without intermediate formation of the hemiketal acid salt). For such purposes 10 grams of the hemiketal were added to 30 ml of dry, liquid hydrogen fluoride, and the mixture was stirred for 3.5 hours at 0° C. The hydrogen fluoride was evaporated off to obtain the dehydrated product in the form of the hydrofluoride salt.

The crude hydrofluoride product was purified by dissolving the same in water, and adding 70% perchloric acid dropwise to precipitate perchloride salt therefrom. Alternatively, the crude hydrofluoride was purified by dissolving the same in acetone, and precipitating the product as the hydriodide salt by the addition of 47% hydriodic acid.

The 11a-chloro-6-methylene-5-oxytetracycline was thereafter 11a-dehalogenated in aqueous solution in the presence of hydrochloric acid and zinc dust. 12 grams of the dehydrated product (in the form of the hydriodide) were thus dissolved in 300 ml of 0.7% HCl and 4 grams of zinc dust were added thereto at room temperature. After stirring for 10-15 minutes the zinc was removed by filtration, the filtrate adjusted to a pH of 0.6–0.8 and extracted with butanol. The butanol extract was concentrated under reduced pressure and the residue triturated with ether and recrystallized from methanol-acetone-concentrated HCl-ether to obtain the product as the partial ester. 5.8 grams of the product were thus obtained, corresponding to a yield of 26% as the methacycline hydrochloride.

For purposes of further comparison an additional sample of hemiketal base was prepared as described in Example XV of the above Blackwood et al patent, reacting the proportions of anhydrous oxytetracycline base and N-chlorosuccinimide in 1,2-dimethoxyethane as specified in the last experiment. After the initial precipitation, the remaining filtrate was poured into 1500 ml of ethyl ether, rather than water, in an effort to increase product yield. 5.6 grams of product (60% yield) were thus obtained, the product displaying an IR band at 5.7 microns, having a melting point of 175° C. and U.V. maxima at λ266 and λ345. The product thus contained a substantial proportion of the ketonic form of the hemiketal base in addition to the desired enolic form thereof.

By way of summary, the results obtained in Examples I and II above are compared below with those obtained in the preceding experiments involving either the partial crystallization of the hemiketal base, the spontaneous crystallization and subsequent dehydration of such base without formation of the hemiketal hydrochloride, or the use of both such procedures as disclosed in the aforesaid Blackwood et al U.S. Pat. No. 2,984,686. The respective experiments have been compared on the basis of the conversions of the initial oxytetracycline reactant to final methacycline hydrochloride product.

It will be seen from the following tabulation that use of the method of the present invention, involving spontaneous crystallization of the hemiketal base followed by formation of the hemiketal acid salt and subsequent dehydration of the latter material, provides markedly superior product yields and purities as compared with syntheses which do not involve such steps.

| Procedure | Equivalent Conversion | Purity |
| --- | --- | --- |
| Method of the Invention | | |
| Example I | 38.5% | 865 mcg/mg 91.3% |
| Example II | 48.5% | 865 mcg/mg 91.5% |
| Spontaneous Crystallization of Hemiketal Base, Without Formation of Hemiketal Hydrochloride | 29.1% | 860 mcg/mg 88.5% |
| Partial Crystallization of Hemiketal Base, Followed by Formation of Hemiketal Hydrochloride (on total hemiketal base) | 32. % | 865 mcg/mg |
| (on hemiketal base in enol form) | 16.4% | 91.3% |
| Blackwood et al, Example XV | 26. % | — Impure |

It is apparent that various changes may be made in the preferred embodiments described hereinabove without departing from the scope of the present invention. The scope of my improved method for manufacture of 6-methylenetetracycline will rather be apparent from consideration of the following claims.

I claim:

1. In a method for the preparation of methacycline hydrochloride which comprises halogenating oxytetracycline hydrochloride to form the corresponding hemiketal base, 11a-halo-5-oxytetracycline-6,12-hemiketal, dehydrating the hemiketal to form the corresponding 11a-halo-6-methylene-5-oxytetracycline, and converting the 11a-halo-6methylene-5-oxytetracycline to methacycline hydrochloride; the improvement comprising
  a. halogenating the oxytetracycline hydrochloride in solution at sub-ambient temperatures while maintaining the acidity of the reaction mixture between pH 3.0 and 5 to spontaneously crystallize the 11a-halo-5-oxytetracycline-6,12-hemiketal substantially entirely in the enolic form;
  b. reacting the 11a-halo-5-oxytetracycline-6,12-hemiketal base with hydrochloric acid at temperatures of from −10° to 20° C to crystallize the hemiketal hydrochloride, 11a-chloro-5-oxtetracycline-6,12-hemiketal hydrochloride, substantially entirely in the enolic form; and
  c. dehydrating the hemiketal hydrochloride rather than the hemiketal base to the corresponding 11a-halo-6-methylene-5-oxytetracycline.

2. The method of claim 1, in which the oxytetracycline hydrochloride is chlorinated to form 11a-chloro-5-oxytetracycline-6,12-hemiketal in step (a), the hemiketal is converted to 11a-chloro-5-oxytetracycline-6,12-hemiketal hydrochloride in step (b), the hemiketal hydrochloride is dehydrated to 11a-chloro-6-methylene-5-oxytetracycline in step (c), and the latter compound is converted to methacycline hydrochloride.

3. The method of claim 2, in which the oxytetracycline hydrochloride is halogenated with N-chlorosuccinomide in an aqueous medium in the proportion of from 1.5 to 1.8 moles of the N-chlorosuccinomide per mole of oxytetracycline hydrochloride, and in the presence of from 2.4 to 2.6 moles of an organic base to form the 11a-chloro-5-oxytetracycline-6,12-hemiketal in step (a).

4. The method of claim 2, in which the hemiketal hydrochloride is dehydrated and converted to 11a-chloro-6-methylene-5-oxytetracycline hydrofluoride in step (c) and the latter salt is dehalogenated to methacycline hydrochloride.

* * * * *